United States Patent
Popovic et al.

(10) Patent No.: US 12,239,380 B2
(45) Date of Patent: Mar. 4, 2025

(54) CONTROL UNIT, SYSTEM AND METHOD FOR CONTROLLING HYBRID ROBOT HAVING RIGID PROXIMAL PORTION AND FLEXIBLE DISTAL PORTION

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1206 days.

(21) Appl. No.: 16/084,746

(22) PCT Filed: Mar. 17, 2017

(86) PCT No.: PCT/EP2017/056435
§ 371 (c)(1),
(2) Date: Sep. 13, 2018

(87) PCT Pub. No.: WO2017/158180
PCT Pub. Date: Sep. 21, 2017

(65) Prior Publication Data
US 2019/0069955 A1    Mar. 7, 2019

Related U.S. Application Data

(60) Provisional application No. 62/309,758, filed on Mar. 17, 2016.

(51) Int. Cl.
*G06F 17/00* (2019.01)
*A61B 34/10* (2016.01)
(Continued)

(52) U.S. Cl.
CPC .............. *A61B 34/10* (2016.02); *A61B 34/20* (2016.02); *A61B 34/30* (2016.02); *A61B 34/32* (2016.02);
(Continued)

(58) Field of Classification Search
CPC ......... A61B 34/10; A61B 34/32; A61B 90/37; A61B 34/30; A61B 34/20;
(Continued)

(56) References Cited

U.S. PATENT DOCUMENTS

| | | | | |
|---|---|---|---|---|
| 6,246,898 B1 * | 6/2001 | Vesely | ..................... | G01H 3/00 600/424 |
| 6,468,265 B1 * | 10/2002 | Evans | .................... | A61B 34/32 600/103 |

(Continued)

FOREIGN PATENT DOCUMENTS

| | | | | |
|---|---|---|---|---|
| CA | 2707755 C | * | 10/2013 | ........... A61F 2/2418 |
| CN | 103108597 A | * | 5/2013 | ............. A61B 18/24 |

(Continued)

*Primary Examiner* — Ronnie M Mancho (57) ABSTRACT

A control unit for a robot system including a robot with a rigid proximal portion having a remote center of motion (RCM), a flexible distal portion, and an image acquisition device. The control unit includes a processor that receives images from the image acquisition device; generates a first deployment path to a first target position based on the images; generates a second deployment path to a second target position from the first target position based on the images; generates first guidance information for positioning the rigid proximal portion along the first deployment path; generates second guidance information for positioning the flexible distal portion along the second deployment path; and deploys the first guidance information to the rigid proximal portion for guiding the rigid proximal portion to the first target position, and deploys the second guidance (Continued)

information to the flexible distal portion for guiding the flexible interface distal portion to the second target position.

19 Claims, 5 Drawing Sheets

(51) Int. Cl.
*A61B 34/20* (2016.01)
*A61B 34/30* (2016.01)
*A61B 34/32* (2016.01)
*A61B 90/00* (2016.01)
A61B 34/00 (2016.01)

(52) U.S. Cl.
CPC ........ *A61B 90/37* (2016.02); *A61B 2034/107* (2016.02); *A61B 2034/2051* (2016.02); *A61B 2034/2055* (2016.02); *A61B 2034/252* (2016.02); *A61B 2034/301* (2016.02); *A61B 2090/374* (2016.02); *A61B 2090/3762* (2016.02)

(58) Field of Classification Search
CPC ...... A61B 2090/374; A61B 2034/2051; A61B 2034/2055; A61B 2034/301; A61B 2034/107; A61B 2090/3762; A61B 2034/252
USPC .......................................................... 700/245
See application file for complete search history.

(56) References Cited

U.S. PATENT DOCUMENTS

| | | | | |
|---|---|---|---|---|
| 7,130,700 B2* | 10/2006 | Gardeski | ........... | A61M 25/0021 607/116 |
| 7,697,972 B2* | 4/2010 | Verard | ........... | A61B 34/20 600/424 |
| 8,046,052 B2* | 10/2011 | Verard | ........... | A61B 5/743 600/407 |
| 8,182,530 B2* | 5/2012 | Huber | ........... | A61B 17/0057 623/2.11 |
| 8,282,653 B2* | 10/2012 | Nelson | ........... | A61B 34/76 600/417 |
| 8,401,616 B2* | 3/2013 | Verard | ........... | A61B 8/4254 600/407 |
| 8,535,336 B2* | 9/2013 | Trovato | ........... | A61B 17/3421 606/130 |
| 8,764,820 B2 | 7/2014 | Dehdashtian | | |
| 8,784,800 B2* | 7/2014 | Morris | ........... | A61K 35/28 424/9.4 |
| 8,790,396 B2* | 7/2014 | Bergheim | ........... | A61F 2/2427 623/2.11 |
| 9,737,371 B2* | 8/2017 | Romo | ........... | B25J 9/1694 |
| 9,956,042 B2* | 5/2018 | Simaan | ........... | A61B 34/30 |
| 9,956,044 B2* | 5/2018 | Gomez | ........... | A61B 34/35 |
| 9,984,437 B2 | 5/2018 | Thienphrapa | | |
| 10,039,473 B2* | 8/2018 | Zhao | ........... | A61B 34/20 |
| 10,231,788 B2* | 3/2019 | Olson | ........... | A61B 34/71 |
| 10,588,597 B2* | 3/2020 | Zhao | ........... | A61B 34/10 |
| 10,806,535 B2* | 10/2020 | Walker | ........... | A61B 34/37 |
| 10,888,307 B2* | 1/2021 | Popovic | ........... | A61B 17/22012 |
| 11,166,646 B2* | 11/2021 | Allenby | ........... | A61B 10/02 |
| 2008/0177279 A1 | 7/2008 | Sumanaweera | | |
| 2008/0200876 A1 | 8/2008 | Kukuk | | |
| 2009/0171184 A1 | 7/2009 | Jenkins | | |
| 2009/0240259 A1* | 9/2009 | Nelson | ........... | A61B 34/76 606/130 |
| 2010/0114308 A1* | 5/2010 | Maschke | ........... | A61F 2/2427 623/2.37 |
| 2011/0071541 A1 | 3/2011 | Prisco | | |
| 2011/0092810 A1* | 4/2011 | Trovato | ........... | A61M 25/0105 600/424 |
| 2011/0222450 A1* | 9/2011 | Youssef | ........... | H04W 76/27 370/311 |
| 2011/0282151 A1* | 11/2011 | Trovato | ........... | G06T 7/248 600/117 |
| 2012/0221100 A1* | 8/2012 | Huber | ........... | A61B 17/2202 623/2.17 |
| 2013/0090528 A1* | 4/2013 | Ramamurthy | ........... | A61B 34/77 600/117 |
| 2013/0131867 A1* | 5/2013 | Olds | ........... | B25J 9/0084 700/260 |
| 2014/0128882 A1* | 5/2014 | Kwak | ........... | A61B 34/30 901/41 |
| 2014/0296973 A1* | 10/2014 | Bergheim | ........... | A61F 2/2418 623/2.11 |
| 2015/0202015 A1 | 7/2015 | Elhawary | | |
| 2016/0184032 A1* | 6/2016 | Romo | ........... | B25J 9/1682 606/130 |
| 2016/0206260 A1* | 7/2016 | Wakai | ........... | A61B 6/463 |
| 2016/0361159 A1* | 12/2016 | Huber | ........... | A61B 17/3421 |
| 2017/0318854 A1 | 11/2017 | Tan | | |
| 2019/0015056 A1* | 1/2019 | Sato | ........... | A61B 6/12 |

FOREIGN PATENT DOCUMENTS

| | | | | |
|---|---|---|---|---|
| CN | 108095777 B | * | 3/2021 | ........... A61N 5/1077 |
| JP | 2008541797 A | * | 11/2008 | ........... A61M 25/01 |
| KR | 20200042468 A | * | 4/2020 | ........... A61N 1/0587 |
| KR | 102292155 B1 | * | 8/2021 | ........... A61B 10/04 |
| WO | WO-2006041505 A1 | * | 4/2006 | ........ A61B 17/3421 |
| WO | 2008086434 A2 | | 7/2008 | |
| WO | 2009144730 A1 | | 12/2009 | |
| WO | 2014139024 A1 | | 9/2014 | |

\* cited by examiner

CONTROL UNIT, SYSTEM AND METHOD FOR CONTROLLING HYBRID ROBOT HAVING RIGID PROXIMAL PORTION AND FLEXIBLE DISTAL PORTION

BACKGROUND

Steerable devices are often used in minimally invasive surgery to improve a surgeon's dexterity inside the patient. One known steerable device includes multiple joints and tendons at the distal end, and the drive system at the proximal end. The device can further be positioned using a robotic positioner. The robotic positioning allows for tracking of the device motion with respect to anatomy.

Another type of a steerable device used in surgery is a surgical image acquisition device, such as an endoscope, with a deflecting tip, or a robotic endoscope. Such an endoscope is a thin, elongated camera assembly that allows a clinician to view the internal anatomy of a patient without the need to surgically expose the anatomy for a direct view. Endoscopes can fit through narrow natural orifices or small incisions in the skin, resulting in reduced trauma to the patient as compared to visualization and intervention without the aid of an endoscope.

Control of known dexterous devices is challenging. The clinician (e.g., surgeon or other user) has to combine the motion of non-dexterous proximal end, which is usually around a fulcrum point (e.g., entry point to the body), and complex dexterous motion inside the body. An approach to this problem is robotic positioning of the dexterous device which increases footprint in the operating room and increases cost and duration of surgery. This problem is amplified if the proximal end is not within field-of-view of imaging devices (e.g. an endoscope takes images only on the inside of the patient, and the field of view in a portable imaging system, such as a C-arm, is too small to image the entire device and can cause radiation exposure to the operator). In addition, once the position is achieved with the dexterous device, hand tremors and involuntary motion of the hand can cause mis-alignment.

For example, aortic valve replacement is a procedure in which a patient's heart valve is replaced with a prosthetic (artificial) valve. Minimally invasive surgery for valve replacement includes deployment of the artificial valve in the beating heart of the patient through a small incision in the chest. A conventional procedure for aortic valve replacement includes, in part, creating a puncture from outside of the heart through a left ventricle wall of the patient, inserting an introducer sheath through the puncture, passing a balloon catheter through the introducer sheath into the left ventricle, and using a pusher and sleeve to advance the balloon catheter and prosthetic valve mounted thereon so that the prosthetic valve is positioned within the aortic annulus. However, the conventional procedure assumes a manual, straight line deployment of the valve from the surface of the patient (at the small incision), between the patient's ribs, through the heart and to the aortic valve (in a beating heart). This is very challenging for a number of reasons. For example, a straight line is a poor approximation of the anatomical environment. That is, there are three primary locations of interest for an aortic valve replacement: a patient entry location, a heart entry location, and the location of the valve itself. These three primary locations are not co-linear. Also, deployment along a straight line may be constrained by other anatomical features, such as ribs, heart muscle, trabeculations inside the heart, and the like. In addition, it is difficult for the surgeon to map all anatomical landmarks in order to plan the straight line path, especially under poor visual feedback and where the anatomy is constantly moving (e.g., heart beating and valve flapping). Further, a field of view of X-ray and ultrasound is typically limited to image the heart only, so there is no image guidance outside the heart.

Accordingly, it maybe desirable to provide an apparatus, systems, methods, and computer-readable storage medium for control of a surgical robot having a rigid proximal portion and a flexible distal portion using a combination of medical imagery and tracking information.

SUMMARY

According to a representative embodiment, a control unit is provided for a robot system that includes a robot with a rigid proximal portion having a remote center of motion (RCM), a flexible distal portion, and an image acquisition device. The control unit includes a processor that receives images from the image acquisition device; generates a first deployment path to a first target position based on the images; generates a second deployment path to a second target position from the first target position based on the images; generates first guidance information for positioning the rigid proximal portion along the first deployment path; generates second guidance information for positioning the flexible distal portion along the second deployment path; and deploys the first guidance information to the rigid proximal portion for guiding the rigid proximal portion to the first target position, and deploys the second guidance information to the flexible distal portion for guiding the flexible distal portion to the second target position.

According to another representative embodiment, a robot system includes a robot and a control unit. The robot comprises a rigid proximal portion having a remote center of motion (RCM), a flexible distal portion, and at least one image acquisition device. The control unit is configured to receive images from the at least one image acquisition device, to generate a first deployment path to a first target position based on the images, to generate a second deployment path to a second target position from the first target position based on the images, to generate first guidance information for positioning the rigid proximal portion along the first deployment path, and to generate second guidance information for positioning the flexible distal portion along the second deployment path.

According to another representative embodiment, a non-transitory computer-readable storage medium is provided, having stored therein machine readable instructions configured to be executed by a processor to control a robot system. The robot system has a control unit and a robot with a rigid proximal portion having a RCM, a flexible distal portion and at least one image acquisition device. The machine readable instructions are configured to perform a method of controlling the rigid proximal portion and the flexible distal portion of the robot to access a target, the method including generating a first deployment path for the rigid proximal portion to a region of interest within a surgical site of a patient; moving the rigid proximal portion on first deployment path to the region of interest; deploying the flexible distal portion through the rigid proximal portion; tracking a position of the flexible distal portion within the region of interest; generating a second deployment path for flexible distal portion to the target; and moving the flexible distal portion on second deployment path to the target.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

It is to be understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms "a", "an" and "the" comprises both singular and plural referents, unless the context clearly dictates otherwise. Thus, for example, "a device" includes one device and plural devices.

As used herein, the statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements" relationships to one another, as illustrated in the accompanying drawings. These terms/phrases are intended to encompass different orientations of the device and/or elements in addition to the orientation depicted in the drawings.

Relative terms, such as "above," "below," "top," "bottom," "upper" and "lower" may be used to describe the various elements" relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be "below" that element. Similarly, if the device were rotated by 90° with respect to the view in the drawings, an element described "above" or "below" another element would now be "adjacent" to the other element; where "adjacent" means either abutting the other element, or having one or more layers, materials, structures, etc., between the elements.

As used in the specification and appended claims, and in addition to their ordinary meanings, the terms 'substantial" or 'substantially" mean to with acceptable limits or degree. For example, 'substantially cancelled" means that one skilled in the art would consider the cancellation to be acceptable.

Figure 1A:
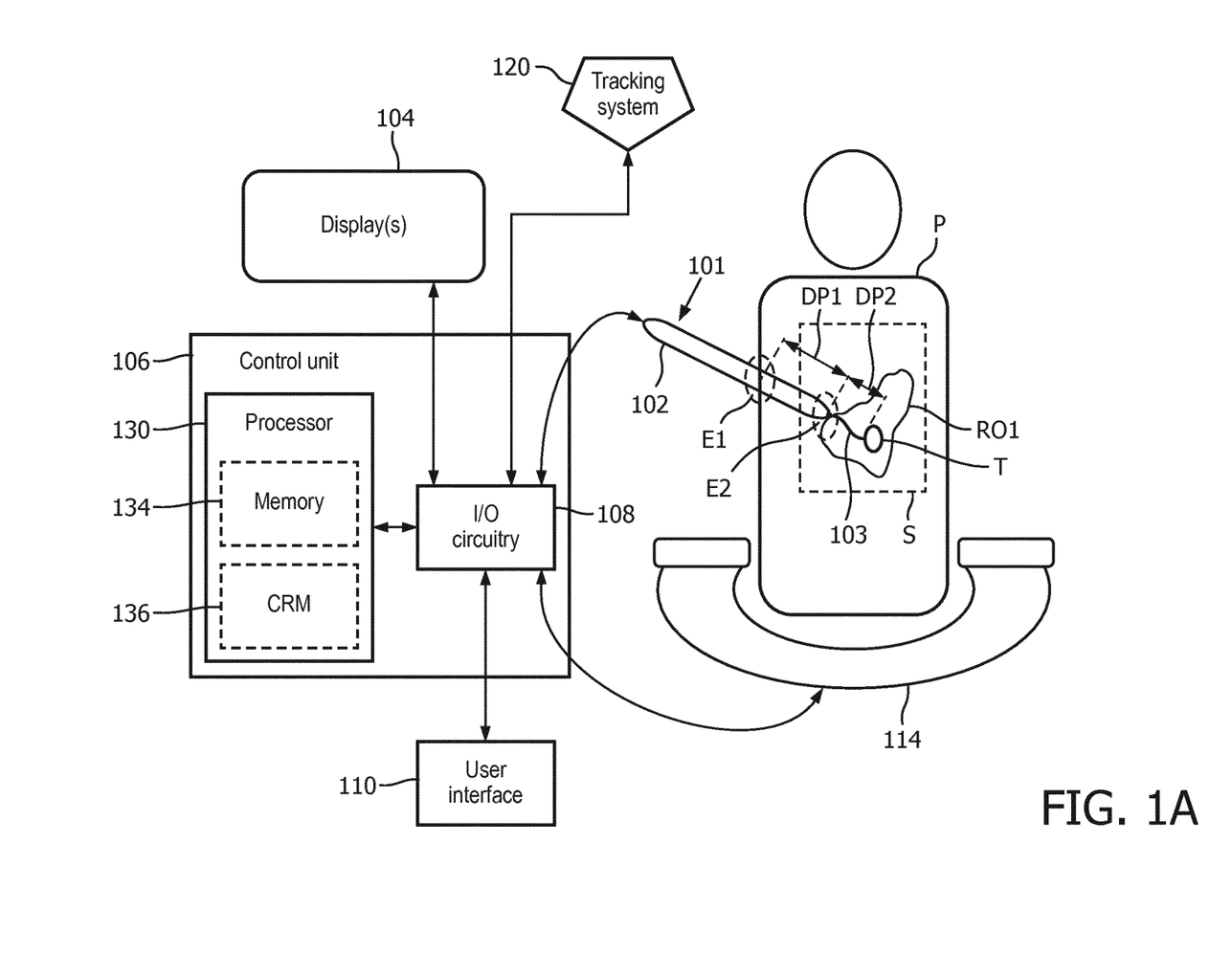
FIG. 1A is a schematic block diagram illustrating a surgical robot system, in accordance with a representative embodiment.

Referring initially to FIG. 1, a surgical robot system 100 in accordance with features of the present teachings will be described. In particular, the surgical robot system 100 may be utilized for medical procedures including, but are not limited to, minimally invasive cardiac surgery, such as coronary artery bypass grafting and mitral valve replacement; minimally invasive abdominal surgery, such as laparoscopy to perform prostatectomy or cholecystectomy; and natural orifice translumenal endoscopic surgery, for example.

FIG. 1A schematically illustrates the surgical robot system 100 comprising a hybrid robot 101 having a rigid proximal portion 102 and a flexible distal portion 103. Generally, the rigid proximal portion 102 is advanced into a body cavity of the patient P through a first entry location E1 at the surface of the patient's body. The rigid proximal portion 102 is guided using imagery to a region of interest ROI (e.g., an internal organ, such as the patient's heart) at a surgical site S, and the flexible distal portion 103 is deployed from the rigid proximal portion 102 into the region of interest ROI through a second entry location E2 (also referred to as a first target position). The flexible distal portion 103 is then guided using imagery to a target T (e.g., a feature or object present in the internal organ, such as an aortic valve of the patient's heart) (also referred to as a second target position) in the region of interest ROI. Once at the target T, the flexible distal portion 103 is able to perform a variety of diagnostic, surgical or treatment procedures (e.g., such as aortic valve replacement). The rigid proximal portion 102 and the flexible distal portion 103 of the robot 101 may be operated under control of a control unit 106, as discussed below, or in an embodiment, the rigid proximal portion 102 may be a handheld introducer manually positioned at the first entry location E1 to the body of the patient P and manipulated by the clinician (user).

The rigid proximal portion 102 of the robot 101 may have a remote center of motion (RCM) at the first entry location E1, enabling the rigid proximal portion 102 to pivot around the first entry location E1 ("pivot point"). In other words, the RCM located at the surface of the body of the patient P, and is configured for movement along a number of degrees of freedom. In an alternative embodiment, the rigid proximal portion 102 of the robot 101 may have a RCM at the second entry location E2, such that the RCM is located at the surface of the ROI, enabling movement along a number of degrees of freedom. In the embodiment where the RCM is locate at the surface of the body P, the opening at the first entry location E1 may be smaller than in the embodiment where the RCM is located at the surface of the ROI. This is because, when the RCM is located at the surface of the ROI, the rigid proximal portion 102 pivots inside the patient P, and thus there must be room at the first entry location E1 for the rigid proximal portion 102 to move distances at the surface of the body of the patient P corresponding to the angle of the movement and the distance between the first entry location E1 and the second entry location E2. In the various embodiments, the rigid proximal portion 102 is manipulated by instructions from the control unit 106, received via an input/output (I/O) circuit 108, or manipulated manually by the clinician, to guide the rigid proximal portion 102 to the desired region of interest ROI in the surgical site S.

In accordance with the present teachings, movement of the rigid proximal portion 102 is tracked, and based on this movement, the location of the distal portion 103 can be adjusted to ensure accurate location of the distal portion 103 relative to the target T. The proximal portion 102 illustratively comprises a tubular portion through which the flexible distal portion 103, as well as components useful in effecting the particular surgical or therapeutic procedure, can be guided. By way of example, such components may include various end-effectors, imaging devices, and other components or devices (e.g., prosthetic heart valves or stents) that can be fed through the proximal portion 102.

The surgical robot system 100 comprises a display 104, which provides real-time images of the location of at least a portion of the rigid proximal portion 102 and the flexible distal portion 103 of the robot 101 within the patient P. The display 104 may receive the real-time images from the image acquisition device 114, via the I/O circuitry 108 and/or a processor 130, as described more fully below. The image acquisition device 114 may be configured to acquire a live image or live images of the proximal portion 102 and the flexible distal portion 103, the flexible distal portion 103, the region of interest ROI (e.g., an anatomical object, such as the heart or another organ) and/or the target T (e.g., a location within or a part of the anatomical object) at the surgical site S.

The image acquisition device 114 may comprise a C-arm, for example, which is an imaging scanner intensifier, so named because of its C configuration. A C-arm has radiographic capabilities, and may be used for fluoroscopic imaging during surgical procedures, as is would be apparent to those skilled in the art. More generally, the image acquisition device 114 may comprise one of a variety of interoperative imaging devices within the purview of one of ordinary skill in the art to provide real-time imaging. These real-time (i.e., inter-operative) images may be used in connection with the pre-operative images to effect registration as described below. Contemplated imaging devices for the second image acquisition device 114 include, but are not limited to computed tomography (CT) devices, ultrasound imaging devices, magnetic resonance imaging (MRI) devices, positron emission tomography (PET) devices, single-photon emission computed tomography (SPECT) imaging devices. These images may be acquired real-time.

Generally, the flexible distal portion 103 comprises at least two links, and at least one joint therebetween. As described more fully below in connection with representative embodiments, the robot 101 is structurally configured to control one or more joints of the flexible distal portion 103 for maneuvering in one or more degrees of motion, e.g., within the region of interest ROI. Illustratively, the flexible distal portion 103 may be one of a number of devices, including but not limited to a two-linkage, one joint device, a snake-like device, or a steerable catheter. In practice, as would be appreciated by those skilled in the art, the flexible distal portion 103 is configured to move in one or more degrees of freedom. Generally, the flexible distal portion 103 linearly advances (i.e., one degree-of-freedom), move in a plane (i.e., two degrees-of-freedom), and rotate. More generally, the flexible distal portion 103 may have a plurality of degrees-of-freedom, e.g., six (6) or more in the case of snake like robots.

By way of example, the flexible distal portion 103 comprises a plurality of links and joints, which are controlled to properly locate a distal end 103' of the flexible distal portion 103 in a desired location (e.g., target T). An example of the flexible distal potion 103 as a multiple link, multiple joint device is depicted in FIG. 1B.

Figure 1B:
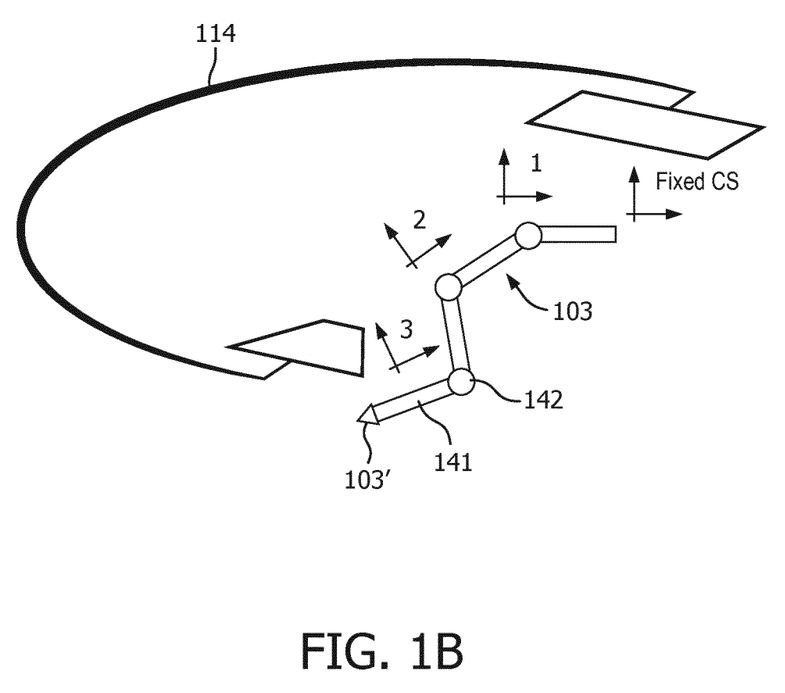
FIG. 1B is a perspective view of a flexible distal portion of a robot in a surgical robot system, in accordance with a representative embodiment.

Referring to FIG. 1B, the flexible distal portion 103 is a snake-like robot portion of the robot 101 according to a representative embodiment comprises a plurality of links 141, each connected by a respective joint 142. Each of the plurality of links 141 comprises a rigid segment, and each of the joints 142 may comprise a geared assembly. Illustratively, each joint 142 can be implemented between one and three degrees of freedom (roll, pitch, and yaw). As described more fully below, the control unit 106 is configured to perform motor control and collect position and orientation data of the flexible distal portion 103. Alternatively, the flexible distal portion 103 may be a catheter robot, such as described, for example, by Wallace et al., U.S. Pat. No. 8,409,136 (Apr. 2, 2013), the disclosure of which is hereby specifically incorporated by reference.

As will be appreciated, the flexible distal portion 103 may comprise an end-effector (not shown) as desired for the particular robotic procedure. By way of example, the end-effector connected to the flexible distal portion 103 may comprise a gripper or a tool holder. Similarly, the flexible distal portion 103 may comprise a tool such as a laparoscopic instrument, laparoscope, a tool for screw placement, a forward-looking camera, or a needle for biopsy or therapy. Other surgical devices and tools within the purview of one of ordinary skill in the art are also contemplated to be used with the flexible distal portion 103.

The display 104 comprises an output device and/or a user interface adapted for displaying images and data, as described more fully herein. The display 104 may include one or more displays that may be co-located near the clinician positioned adjacent to various elements of the surgical robot system 100. The display 104 is configured to display live and/or preoperative images of the surgical site S provided, for example, by the image acquisition device 114. The display 104 may output visual, audio, and/or tactile data. Examples of the display 104 include, but are not limited to, a computer monitor, a television screen, a touch screen, tactile electronic display, Braille screen, cathode ray tube (CRT), storage tube, bistable display, electronic paper, vector display, flat panel display, vacuum fluorescent display (VF), light-emitting diode (LED) displays, electroluminescent display (ELD), plasma display panels (PDP), liquid crystal display (LCD), organic light-emitting diode displays (OLED), a projector, and a head-mounted display (HMD).

The control unit 106 is configured to receive input from various components of the surgical robot system 100, and to provide outputs (e.g., instructions or commands) thereto. The control unit 106 comprises the I/O circuitry 108, which receives inputs from various components of the surgical robot system 100, and provides outputs to and receives inputs from the processor 130, as is described more fully below. The processor 130 also comprises a memory 134 for enabling processing and a computer readable medium (CRM) 136 (which may be the same or separate memories). The processor 130 is generally configured to receive images, e.g., from the image acquisition device 114, via the I/O circuitry 108, and to process and store the acquired images in the memory 134 and/or the CRM 136. The processor 130 is therefore able to build a database essentially visually mapping interior portions of the patient P captured by the image acquisition device 114. In alternative embodiments, an additional image acquisition device may be included to provide internal images. Such additional image acquisition devices may include, for example, a transesophageal echocardiography (TEE) probe or an endoscope, and the internal images may include interior portions of the patient P traversed by the additional image acquisition device. The database built by the processor 130 may be used to determine paths from the first entry location E1 to the second entry location E2 (e.g., a first deployment path DP1 to a first target position), and from the second entry location E2 to the target T within the region of interest ROI (e.g., a second deployment path DP2 to a second target position). The processor 130 transmits the images to the display 104 via the I/O circuitry 108 for display.

When an additional image acquisition device comprises an endoscope (not shown), it provides endoscopic images. The endoscope may be controlled by an endoscopic controller, operated independently or under control of the control unit 106. In certain representative embodiments, the endoscope may include a tube, and a light delivery system to illuminate the organ or object under inspection, for example, the light source is normally outside the body and the light is typically directed via an optical fiber system. Also included may be a lens system transmitting the image from the objective lens to the viewer, typically a relay lens system in the case of rigid endoscopes or a bundle of fiberoptics in the case of a fiberscope. Also contemplated are videoscopes, with no eyepiece, in which a camera transmits images to a screen (e.g., display 104) for image capture. An additional channel of the endoscope may allow entry of medical instruments or manipulators.

Examples of an endoscope for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system. The imaging is local, and surface images may be obtained optically with fiber optics, lenses, or miniaturized (e.g. CCD based) imaging systems.

The additional image acquisition device may be connected to, and may be a component of the control unit 106. The additional image acquisition device provides images ultimately provided to the display 104, and may include any type of camera having a forward optical view or an oblique optical view, and may be capable of acquiring a sequence of two-dimensional digital video frames at a predefined frame rate (e.g., 30 frames per second) and capable of providing each digital video frame to the control unit 106 via the I/O circuitry 108. In particular, the additional image acquisition device may be positioned and oriented such that within its field of view it can capture images of the flexible distal portion 103. In some embodiments, additional image acquisition device includes a camera which is actuated by a motor and can be positioned along a planned instrument path for the robot 101.

The processor 130 may comprise one or more microprocessors that may be programmed using software (e.g., microcode) to perform various functions discussed herein. Notably, the processor 130 may comprise more than one processor or processing core. The processor 130 may for instance be a multi-core processor. The control unit 106 may also comprise a collection of processors within a single computer system (not shown) or distributed among multiple computer systems (not shown) associated with the surgical robot system 100. As will be appreciated, many programs have their instructions performed by the processor 130 that may be within the same computing device or which may even be distributed across multiple computing devices. Examples of components that may be employed as the processor 130 in various embodiments of the present disclosure include, but are not limited to, conventional microprocessors, microcontrol units, application specific integrated circuits (ASICs), and/or field-programmable gate arrays (FPGAs).

The memory 134 and/or the CRM 136 may be configured to store various types of data gathered during the course of the function of the various components of the surgical robot system 100. These data include image data and tracking data gathered as described more fully below. The memory 134 and/or the CRM 136 may also store pre-operative data, such as pre-operative image data. As described more fully below, these data can be used to track the locations of the rigid proximal portion 102 and the flexible distal portion 103 during operation of the robot 101. Furthermore, each of the memory 134 and the CRM 136 comprises a non-transitory computer readable medium, which stores machine readable instructions configured to be executed by the processor 130 to control the surgical robot system 100, and to store various data, including image data and tracking data. By way of example, these instructions (programs) are encoded in the memory 134, and when executed on the processor 130, perform at least some of the functions discussed herein. Notably, the terms "program" or "computer program" are used herein in a generic sense to refer to various types of computer code (e.g., software or microcode) that can be employed to program the control unit 106.

The memory 134 and the CRM 136 may comprise non-volatile computer memory, or volatile computer memory, or both, including, but not limited to: such as random-access memory (RAM), read-only memory (ROM), programmable read-only memory (PROM), electrically programmable read-only memory (EPROM), electrically erasable and programmable read only memory (EEPROM), universal serial bus (USB) drive, floppy disks, compact disks (CDs), optical disks, magnetic tape, etc.), a smart card, a digital video disc (DVD), a CD-ROM, and a solid state hard drive. Various storage media, such as the memory 134, for example, may be fixed within the processor 130 or may be transportable, such that the one or more programs stored thereon can be loaded into the processor 130 so as to implement various aspects of the present teachings discussed herein.

The robot 101 introduces an additional coordinate system, and therefore alignment (position and orientation) of the robot 101 with some desired frame of reference is difficult to guarantee and maintain because it is positioned with workspace and motion constraints. As described more fully below, misalignment of disparate coordinate systems so that the same alignment need not be performed mentally by clinicians is effected using known registration methods and apparatuses. To this end, a variety of current methods and apparatuses exist to register the robot 101 and the particular components thereof to the imaging system. By way of example, registration can be performed by matching features of the flexible distal portion 103 visible in the images with corresponding features gathered preoperatively. The target T may be identified by the clinician or surgeon by marking the location of the target T in the images. In another embodiment, the target T can be automatically detected by means of feature matching and object recognition known in art. The target T may then be computed from the image to the robot coordinate system using registration. Examples of registration are described in commonly owned U.S. Pat. No. 9,095,252 by Popovic (Aug. 4, 2015); and U.S. Patent Application Publications 2011/0282151 by Trovato et al. (Nov. 17, 2011), 2014/0212025 by Thienphrapa et al. (Jul. 31, 2014), 2015/0010225 by Popovic et al., 2015/0073265 (Jan. 8, 2015), 2015/0126859 by Popovic et al. (May 7, 2015), and 2015/0202015 by Elhawary et al. (Jul. 23, 2015), all of which are hereby specifically incorporated by reference.

A tracking system 120 is configured to generate tracking information with respect to the rigid proximal portion 102 and the flexible distal portion 103 of the robot 101. The tracking system 120 may be one or more of an optical tracking system, mechanical tracking system, an electromagnetic tracking system, and a shape sensing tracking system, as would be appreciated by those skilled in the art. A sensor or tag, such as a radio frequency (RF) sensor, LED sensor, passive markers, reflective markers, may be included at the proximal portion 102 of the robot 101, or proximal to the end 103' of the flexible distal portion 103, or both to cooperate with the tracking system 120. Shape sensing tracking systems are described, for example, by Ramamurthy et al., U.S. Pat. No. 9,186,046 the disclosure of which is hereby specifically incorporated by reference.

The tracking system 120 provides information to the control unit 106 to provide feedback of the current position of the rigid proximal portion 102 and the flexible distal portion 103. This allows adjustment of the position of the rigid proximal portion 102 relative to the region of interest ROI, and adjustment of the position of the flexible distal portion 103 relative to the target T. Through tracking of the rigid proximal portion 102 and the flexible distal portion 103, and data from the registration realized by the image acquisition device 114, the processor 130 is configured to ultimately determine the location of the flexible distal portion 103 relative to the target T. Notably, software in the memory 132, for example, enables the calculation by the processor 130 of the current location of the flexible distal portion 103 relative to the target T. Based on these calculations, the processor 130 provides instructions/commands to the flexible distal portion 103 to move as needed to be in better position relative to the target T. In one embodiment, these commands function to compensate for tremor-induced motion in the rigid proximal portion 102 or from the clinician's hands to compensate (and substantially nullify) any undesired movement by the flexible distal portion 103.

The surgical robot system 100 comprises a user interface 110. The user interface 110, like the display 104, is illustratively coupled to the control unit 106 via a hardware interface (not shown) and the I/O circuitry 108. The hardware interface enables the processor 130 to interact with various components of the surgical system, as well as control an external computing device (not shown) and/or apparatus. The hardware interface may allow a processor to send control signals or instructions to various components of the surgical robot system 100, as well as an external computing device and/or apparatus. The hardware interface may also enable a processor to exchange data with various components of the surgical robot system 100, as well as with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

The user interface 110 allows the clinician to interact with surgical robot system 100 through a computer (not shown) or computer system (not shown). The user interface 110 may comprise, for example, a touch screen, a keyboard, a mouse, a trackball and/or touchpad. Generally, the user interface 110 may provide information or data to the clinician and/or receive information or data from the clinician. The user interface 110 may be configured to receive input from the clinician to be received by the computer, and may provide output to the user from the computer. In other words, and as will become clearer, the user interface 110 may be configured to enable the operator to control or manipulate the computer, and the user interface 110 may be configured to allow the computer to indicate the effects of the clinician's control or manipulation. The display of data or information on the display 104 or a graphical user interface thereof, is an example of providing information to the clinician. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of components of the user interface 110, which enable the receiving of information or data from an operator.

As noted above, the control unit 106 comprises I/O circuitry 108. Among other functions, the I/O circuitry 108 controls communication to elements and devices external to the control unit 106. The I/O circuitry 108 acts as an interface including necessary logic to interpret input and output signals or data to/from the processor 130. For example, the I/O circuitry 108 may include a first input configured to receive the medical imagery, such as from the image acquisition device 114, related to rigid proximal portion 102 and the flexible distal portion 103 of the robot 101 at or near the surgical site S, and a second input configured to receive the tracking information of the proximal portion 102 and the flexible distal portion 103 of the robot 101 from the tracking system 120. The I/O circuitry 108 may include an output configured to provide the medical imagery related to the robot 101 to a display of the display 104.

Representative embodiments may also be directed to a non-transitory computer-readable storage medium (e.g., memory 134/CRM 136) having stored therein machine readable instructions configured to be executed by the processor 130 to control the surgical robot system 100 including the robot 101 having the proximal portion 102 to be positioned at an entry to a patient's body and the flexible distal portion 103 to be positioned at a surgical site S within the patient's body. The machine readable instructions are stored in memory 132 and configured to perform a method 500 to compensate for motion of the handheld introducer 102.

For purposes of illustration, it may be assumed that the region of interest ROI is the patient's heart, for example. In this case, the position of the end 103' of the flexible distal potion 103 may be determined by the clinician by images provided at the display 104. As such, an end-effector disposed at the end 103' may be used to make an incision at a precise location of the heart (region of interest ROI) at the second entry location E2. The clinician can then further guide the end 103' of the flexible distal portion 103 to the location of the aorta valve (target T) to be replaced. The valve can then be replaced, again with the precision location of the heart being determined by the control unit 106 using the various image acquisition and registration methods described above.

Based on data from the tracking system 120 alone, or in combination with data from the second image acquisition device 114, the processor 130 can compensate for sporadic movement (e.g., induced by clinician tremor) of the proximal portion 102 through commands to the flexible distal portion 103 of the robot 101 so that substantially nullifying movement of the flexible distal portion 103 can negate the tremor at the end 103' of the flexible distal portion 103. In a representative embodiment, in a position compensation mode, an image related to the flexible distal portion 103 is taken using the image acquisition device 114. As noted above, the image may be an X-ray image, cone-beam CT image, an ultrasound image, or an endoscopic image. The shape and pose of the flexible distal portion 103, and/or registration within the surgical site S, is thereby determined and may be shown on the display 104. For example, real-time tracking of surgical tools relative to a pre-operative surgical plan and interoperative images involving an image-based registration and tool tracking registration are disclosed in above-referenced U.S. Patent and Patent Application Publications. Since anatomy is visible in the image, the relative position of the flexible distal portion 103 with respect to the anatomy is also known, and the flexible distal portion 103 can be used to reach the anatomical target T (in this example the location of the valve to be replaced) using the position computed by the control unit 106.

In order to keep the flexible distal portion 103 in the same position for the duration of procedure, such as biopsy or heart ablation, in a manner described above, the control unit 106 continuously updates the position of the proximal portion 102 of the robot 101 from the tracking system 120 using tracking information from the tracking system 120, and possibly the image acquisition device 114. In other words, the flexible distal portion 103 is controlled to move inside the patient P to compensate for motion of the rigid proximal portion 102 on the outside of the patient P.

In a representative embodiment, the control unit 106 may compute robot 101 motion parameters of joints (e.g., joints 142) of the flexible distal portion 103 in response to a defined entry location, a defined second deployment path DP2, and the anatomical target T. Such parameters may align the flexible distal portion 103 to the defined second entry location E2 of the heart muscle and the planned second deployment path DP2. The control unit 106 may produce control commands in response to the computed joint motion parameters, which align flexible distal portion 103 to the planned second entry location E2 and the second deployment path DP2, and communicate the robot control commands to the robot 101.

The processor 130 may perform the described functions and operations using a combination of hardware, software and firmware. The processor 130 is configured to process images, such as from the image acquisition device 114, related to the rigid proximal portion 102 and the flexible distal portion 103 at or near the surgical site S to register the flexible distal portion 103 with corresponding anatomy at the surgical site S. As described in connection with FIGS. 2A and 2B, the processor 130 is configured to process the tracking information of the proximal portion 102 of the robot 101 from the tracking system 120 to determine motion around the RCM. The processor 130 may be further configured to transmit the images to the display 104 via the I/O circuitry 108.

As can be appreciated from the description above, through the coordinated function of the image acquisition device 114, the tracking system 120, the various data and software stored in memory 134/CRM 136 and the actions of the processor 130, the control unit 106 is configured to provide one or more control commands to control the acquisition and processing of live and preoperative images related to the flexible distal portion 103 of the surgical robot 101 at the surgical site S, and the target T, and use tracking information related to the proximal portion 102 and/or the flexible distal portion 103 of the robot 101 to further control the flexible distal portion 103 relative to the target T. In the illustrative examples described below, various features of the surgical robot system 100 of representative embodiments are further described. It is noted that these examples are merely illustrative, and in no way intended to be limiting.

Figure 2A:
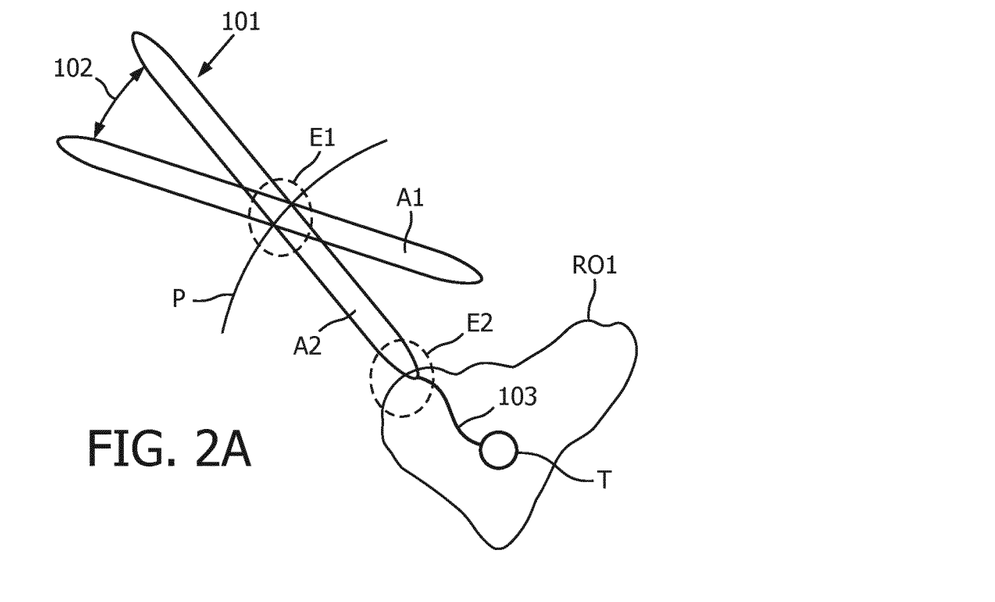
FIG. 2A is a schematic diagram illustrating details of operating the robot in the surgical robot system shown in FIG. 1A, in accordance with a representative embodiment.
Figure 2B:
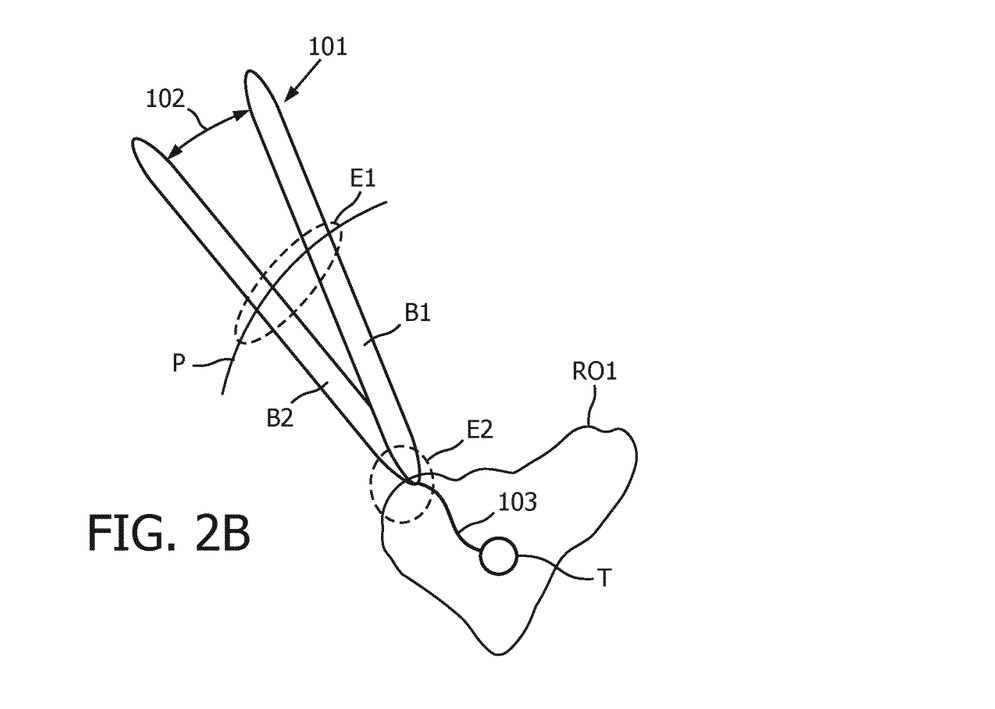
FIG. 2B is a schematic diagram illustrating details of operating the robot in the surgical robot system shown in FIG. 1A, in accordance with a representative embodiment.

FIGS. 2A and 2B are schematic diagrams illustrating details of operating the robot in the surgical robot system shown in FIG. 1A, in accordance with representative embodiments. In particular, FIG. 2A illustrates operation of the robot where the RCM of rigid proximal portion 102 is located at the surface of the patient's body, and FIG. 2B illustrates operation of the robot where the RCM of rigid proximal portion 102 is located at the surface of the region of interest ROI (e.g., internal organ).

Referring to FIG. 2A, the rigid proximal portion 102 of the robot 101 is inserted into the patient P through first entry location E1 (e.g., surgical port), either under control of the control unit 106 or manually. The RCM of the rigid proximal portion 102 is located at the first entry location E1 on the surface of the patient's body, enabling the rigid proximal portion 102 to pivot among various angles (e.g., A1 and A2) relative to the surface of the patient's body, thereby positioning the rigid proximal portion 102 to accommodate access by the flexible distal portion 103 to the target T in the region of interest ROI (e.g., an internal organ). The rigid proximal portion 102 may be inserted into the region of interest ROI through second entry location E2. Once inserted, the flexible distal portion 103 is deployed to access the target T.

In an embodiment, a processor (e.g., processor 130 in FIG. 1A) receives images from at least one image acquisition device (e.g., image acquisition device 114), generates a first deployment path (e.g., first deployment path DP1) based, at least in part, on the received images for the rigid proximal portion 102 to follow from the first entry location E1 to the second entry location E2, and provides instructions for a controller (e.g., control unit 106) to deploy the rigid proximal portion 102 along the first deployment path. The processor also generates a second deployment path (e.g., second deployment path DP2) based, at least in part, on the received images for the flexible distal portion 103 to follow from the second entry location E2 to the target T, and provides instructions for the controller to deploy the flexible distal portion 103 from the end of the rigid proximal portion 102 along the second deployment path.

Referring to FIG. 2B, the operation is similar, except that the rigid proximal portion 102 pivots around the second entry location E2, requiring a larger incision fro the first entry location E1 to accommodate the pivotal movements of the rigid proximal portion 102 at the surface of the patient's body. That is, the rigid proximal portion 102 of the robot 101 is inserted into the patient P through first entry location E1, either under control of the control unit 106 or manually. The RCM of the rigid proximal portion 102 is located at the second entry location E2 on the surface of the region of interest ROI (e.g., an internal organ) within the patient's body, enabling the rigid proximal portion 102 to pivot among various angles (e.g., B1 and B2) relative to the surface of the region of interest ROI, thereby positioning the rigid proximal portion 102 to accommodate access by the flexible distal portion 103 to the target T in the region of interest ROI.

As described above, in an embodiment, a processor (e.g., processor 130) receives images from at least one image acquisition device (e.g., image acquisition device 114), generates a first deployment path based, at least in part, on the received images for the rigid proximal portion 102 to follow from the first entry location E1 to the second entry location E2, and provides instructions for a controller (e.g., control unit 106) to deploy the rigid proximal portion 102 along the first deployment path. The processor also generates a second deployment path based, at least in part, on the received images for the flexible distal portion 103 to follow from the second entry location E2 to the target T, and provides instructions for the controller to deploy the flexible distal portion 103 from the end of the rigid proximal portion 102 along the second deployment path.

Figure 3:
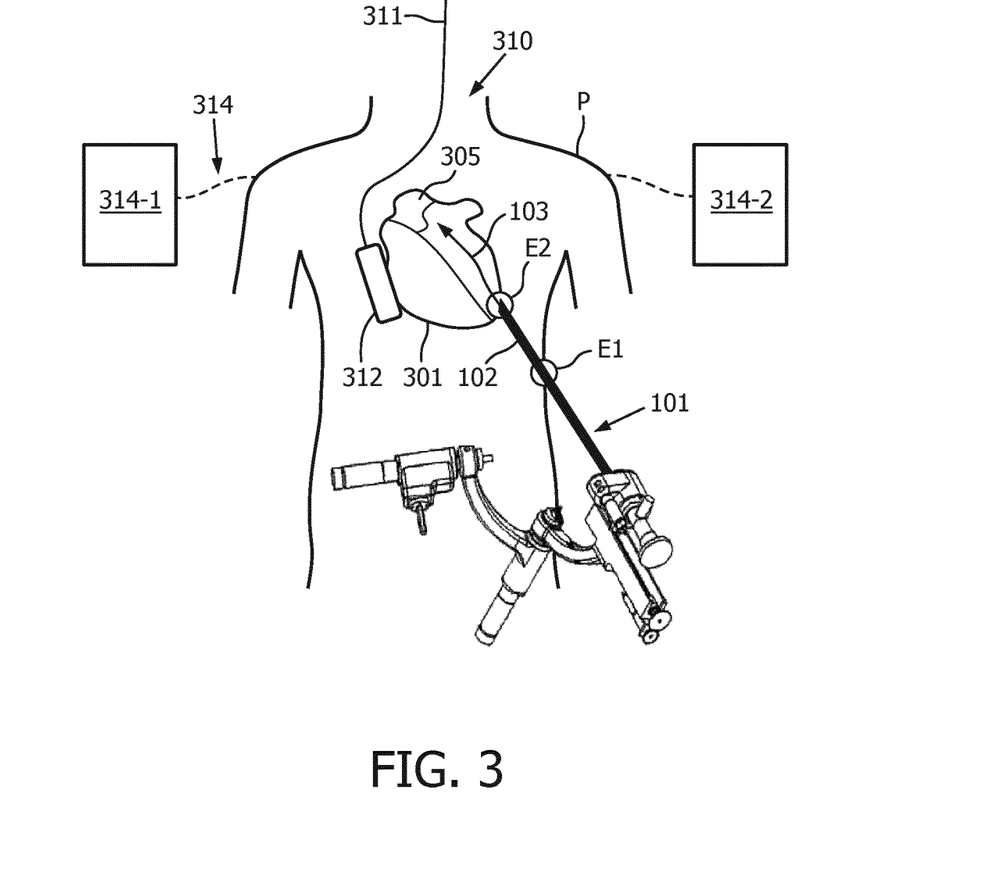
FIG. 3 is a perspective view a surgical robot system for accessing a patient's heart, in accordance with a representative embodiment.

FIG. 3 is a perspective view a surgical robot system for accessing a patient's heart, in accordance with a representative embodiment, in which the surgical robot system is used for an aortic valve replacement. The aortic valve replacement is an example of implementing the surgical robot system 101, which may be used for other types of medical procedures and surgeries without departing from the scope of the present teachings.

Referring to FIG. 3, surgical robot system 301 includes robot 101 with rigid proximal portion 102 and flexible distal portion 103. In the depicted embodiment, the RCM of the rigid proximal portion 102 is at the surface of the body of patient P. The rigid proximal portion 102 is manipulated, e.g., by a controller or manually, through first entry location E1 (e.g., an initial incision is made between two ribs) and enters the heart 301 through second entry location E2. The flexible distal portion 103 deploys through the rigid proximal portion 102, and is used to deploy a prosthetic valve into ventricle 305.

The surgical robot system 301 further includes image acquisition device 314, which is a C-arm imaging system with image detector 314-1 and source 314-2. The image acquisition device 314 provides live and/or preoperative images of the heart 310 and the robot 101. The image data, together with tracking data from a tracking system (e.g., tracking system 120) enable a processor (e.g., processor 130) to determine and monitor deployment paths for the rigid proximal portion 102 to follow from the first entry location E1 to the second entry location E2, and for the flexible distal portion 103 to follow from the second entry location E2 to the ventricle 305 (target). In the depicted embodiment, a transesophageal echocardiography (TEE) probe 310, with probe 311 and transducer 312, is also included to provide live imaging of the heart 301.

Figure 4:
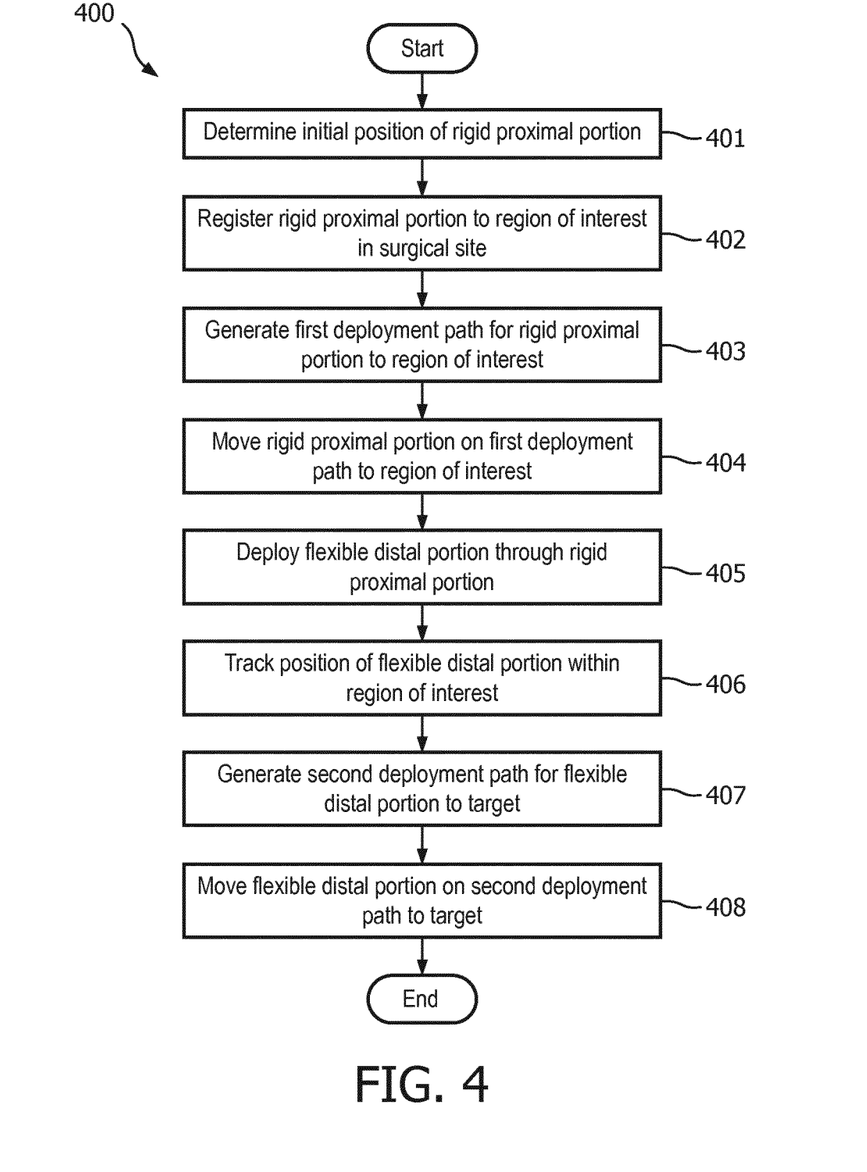
FIG. 4 is a flowchart illustrating various operations in a method of controlling a rigid proximal portion and a flexible distal portion of a robot to access a target, in accordance with a representative embodiment.

FIG. 4 is a flowchart illustrating operations of a method 400 of control and guidance which may be performed by the surgical robot system 100, in accordance with a representative embodiment. To provide an example in the description below, it will be assumed that method 400 is performed by the version of surgical robot system 100 is illustrated in FIG. 1A, thus all or part of the operations depicted in FIG. 4 may be performed by or under control of the processor 130. However, the method may be implemented using other embodiments of the surgical robot system, without departing from the scope of the present teachings.

In this embodiment, it is assumed that the rigid proximal portion 102 is configured such that the RCM is positioned at the first entry point E1 to the patient P (e.g., between the ribs). This configuration minimizes injury to ribs and chest muscles, but somewhat limits motion of the rigid proximal portion 102 to be performed before the flexible distal portion 103 is deployed. In operation 401, an initial position (on the patient's body) of the rigid proximal portion 102 is determined. The rigid proximal portion 102 is aligned with the initial position, e.g., by the clinician, using either manual or master/slave control of the rigid proximal portion, to position the rigid proximal portion 102 in the body cavity through the first entry point E1.

The rigid proximal portion 102 is advanced through the body cavity toward the surgical site S. Once the rigid proximal portion 102 is visible in image(s) provided by the image acquisition device 114, such as x-ray images, the rigid proximal portion 102 is registered to the region of interest ROI (e.g., the patient's heart, in this example) using any method, including registration methods provided herein. For example, real-time tracking of surgical tools relative to a pre-operative surgical plan and intra-operative images involving an image-based registration and tool tracking registration are disclosed in commonly owned U.S. Patent Application Publication 2012/0294498 by Popovic (Nov. 22, 2012), which is hereby specifically incorporated herein by reference.

In operation 403, a first deployment path DP1 is generated for the rigid proximal portion 102 from the RCM (e.g., the first entry location E1) to an entry point of the region of interest ROI (e.g., the second entry location E2). The first deployment path DP1 may be generated by the processor 130 based on known locations of the first entry location E1 and the location of the boundaries of the region of interest ROI, for example, through images provided by the image acquisition device 114. In an embodiment, the first deployment path DP1 may be determined by the clinician, for example, using data and/or images provided by the processor 130 and/or the image acquisition device 114.

The rigid proximal portion 102 is moved along the determined first deployment path DP1 by operation of the robot 101, until the rigid proximal portion 102 is advanced into the region of interest ROI through the second entry location E2, using automatic deployment under control of the control unit 106, in operation 404. For example, first guidance information may be generated for positioning the rigid proximal portion 102 along the first deployment path DP1. Generally, guidance information includes registration of the robot 101 to the image acquisition device 114, and may provide data such as coordinates in a three-dimensional space, corresponding to a determined deployment path within the patient P and commands to maneuver the robot to the coordinates. Alternatively, the clinician may manually move the rigid proximal portion 102 along the determined first deployment path DP1, e.g., using the live images from the image acquisition device 114.

In operation 405, the flexible distal portion 103 is deployed into the region of interest ROI through the rigid proximal portion 102. Since, in the present example, the flexible distal portion 103 is introduced in the heart, it is visible under x-ray and ultrasound. The flexible distal portion 103 may be registered to x-ray from the image acquisition device 114, as well as to ultrasound from an ultrasound TEE probe (optional), such as TEE probe 310 discussed above, using EchoNavigator® available from Philips Electronics, for example, in order to provide close-up live imaging of the heart.

The position of the flexible distal portion is tracked within the region of interest ROI in operation 406. A second deployment path DP2 is generated in operation 407 for the flexible distal portion 103 from the tracked location of the flexible distal portion 103 to the target T (e.g., the heart muscle). The second deployment path DP2 may be generated by the processor 130 based on known locations of the second entry location E2 and the location of the target T, for example, through images provided by the image acquisition device 114.

In operation 408, a distal tip of the flexible distal portion 103 is moved along the second deployment path DP2 to the target T. For example, second guidance information may be generated for positioning the flexible distal portion 103 along the second deployment path DP2 in order to move the flexible distal portion 103. In the present example, the valve annulus of the aortic valve of the heart may be detected in at least one of the x-ray and ultrasound images for generating the second deployment path DP2 and/or the second guidance information, and the flexible distal portion of the robot 101 may be controlled using such live images to position the distal tip of the flexible distal portion at or perpendicular to the annulus. Once the position is reached, the therapy device is deployed. As discussed above, therapy device may include a balloon catheter and a prosthetic valve passed the left ventricle of the heart, and using a pusher and sleeve to advance the balloon catheter and prosthetic valve mounted thereon in order to properly position the prosthetic valve within the aortic annulus.

In an alternative embodiment, the rigid proximal portion 102 is configured such that the RCM is positioned at the second entry location E2 to the region of interest ROI (e.g., the heart). In this embodiment, the first entry location E1 at the chest cavity has to be a larger incision to allow small motion of the rigid proximal portion 102. This enables repositioning of the flexible distal portion 103 once deployed.

The deployment operations are the same as in the embodiment discussed above with reference to FIG. 4. However, in the present embodiment, a last operation is added to facilitate repositioning of the flexible distal portion 103. For example, if the plan for the second deployment path DP2 yields an unreachable path, the rigid proximal portion 102 of the robot 101 may reposition the flexible distal portion device to a reachable position by pivoting around the second entry location E2 to the region of interest ROI.

In certain embodiments, the method 400 may further include transmitting the medical imagery to display 104. The display arrangement is broadly defined herein as any device structurally configured for displaying images and tracked surgical tools and other end-effectors under any suitable technique. Examples of a display include a computer monitor, a television screen, a touch screen, a projector, and head-mounted display (HMD).

The present teachings are part of a technological progression towards smart systems and devices. Possible applications include augmented reality of live video with preoperative CT, surgical navigation, especially in minimally invasive surgery where the workspace is obscured from view, and finding anatomical targets and tumors.

In view of this disclosure it is noted that the various structures and components may be implemented in a variety of means. Further, the various materials, structures and parameters are included by way of example only and not in any limiting sense. In view of this disclosure, those skilled in the art can implement the present teachings in determining their own applications and needed materials and equipment to implement these applications, while remaining within the scope of the appended claims.

What is claimed is:

1. A controller for a robot system, the controller comprising:
   a memory configured to store pre-operative image data; and
   a processor coupled to the memory and configured to control a robot having a rigid proximal portion and a flexible distal portion, the rigid proximal portion (i) comprising a portion through which to insert the flexible distal portion and (ii) having a pivot point configured to provide a plurality of degrees of freedom for movement of the rigid proximal portion at a pre-designated position in a surgical procedure, the processor configured to:
   receive images from at least one image acquisition device;
   receive first tracking information indicating a tracked position of the rigid proximal portion;
   generate a first deployment path to follow from an entry location at a body surface to a first target position that is an entry location to a region of interest within the body based on the received images;
   generate a second deployment path to follow from the first target position at the entry location to the region of interest to a second target position within the region of interest based on the received images;
   generate first guidance information for positioning the rigid proximal portion along the first deployment path based on the first tracking information, the received images, and the pre-operative images;
   guide the rigid proximal portion to be positioned at the first target position at the entry location to the region of interest based on the first guidance information, wherein the rigid proximal portion is configured so that, when the rigid proximal portion is positioned at the first target position, the pivot point of the rigid proximal portion is located at the entry location to the region of interest enabling the rigid proximal portion to pivot around the entry location to the region of interest;
   deploy the flexible distal portion through the rigid proximal portion into the region of interest;
   receive second tracking information for tracking the position of the flexible distal portion;
   generate second guidance information for positioning the flexible distal portion along the second deployment path based on the received images, the pre-operative image data, and the second tracking information; and
   based on the second guidance information guide the deployed flexible distal portion to the second target position within the region of interest, wherein the processor is configured to independently guide the flexible distal portion relative to the rigid proximal portion.

2. The controller according to claim 1, wherein the first target position comprises the entry location of the region of interest in a surgical site within a patient.

3. The controller according to claim 2, wherein the second target position comprises a target within the region of interest in the surgical site.

4. The controller according to claim 3, wherein the region of interest comprises an internal organ of the patient, and the target comprises a location within or a part of the organ.

5. The controller according to claim 3, wherein the pivot point is located at the entry location of the organ at the surgical site.

6. The controller of claim 1, wherein first deployment path is linear and the second deployment path is non-linear.

7. The controller according to claim 1, wherein the first and second guidance information include registration of the robot to the imaging device.

8. A robot system comprising:
a robot comprising:
   a rigid proximal portion having a pivot point configured to provide a plurality of degrees of freedom for movement of the rigid proximal portion at a pre-designated position in a surgical procedure, the rigid proximal portion comprising a portion through
which to insert a flexible distal portion, and
   the flexible distal portion;
a memory configured to store pre-operative image data;
at least one image acquisition device; and
a controller configured to:
   receive images from the at least one image acquisition device;
   receive first tracking information indicating a tracked position of the rigid proximal portion;
   generate a first deployment path to follow from an entry location at a body surface to a first target position that is an entry location to a region of interest within the body based on the received images;
   generate a second deployment path to follow from the first target position at the entry location to the region of interest to a second target position within the region of interest based on the images;
   generate first guidance information for positioning the rigid proximal portion along the first deployment path based on the first tracking information, the received images, and the pre-operative image data;
   guide the rigid proximal portion to be positioned at the first target position at the entry location to the region of interest based on the first guidance information, wherein the rigid proximal portion is configured so that, when the rigid proximal portion is positioned at the first target position, the pivot point of the rigid proximal portion is located at the entry location to the region of interest enabling the rigid proximal portion to pivot around the entry location to the region of interest;
   deploy the flexible distal portion through the rigid proximal portion into the region of interest;
   receive second tracking information indicating a tracked position of the flexible distal portion;
   generate second guidance information for positioning the flexible distal portion along the second deployment path based on the second tracking information, the received images, and the pre-operative image data; and
   based on the second guidance information guide the deployed flexible distal portion to the second target position within the region of interest, wherein the controller is configured to independently guide the flexible distal portion relative to the rigid proximal portion.

9. The robot system according to claim 8, wherein first deployment path is linear and the second deployment path is non-linear.

10. The robot system according to claim 8, wherein the first target position is the entry location to the region of interest within a surgical site of a patient, and the second target position is a location of a target within the region of interest.

11. The robot system according to claim 10, wherein the region of interest is an organ of the patient, and the pivot point is located at the entry location to the organ of the patient.

12. The robot system according to claim 10, wherein the region of interest is a heart of the patient, and the target is an aortic valve to be replaced with a prosthetic valve.

13. The robot system according to claim 12, wherein the at least one image acquisition device comprises:
   a transesophageal echocardiography (TEE) probe having a probe and a transducer located adjacent the heart to provide live imaging of the heart; and
   a C-arm comprising an x-ray for imaging the surgical site.

14. A non-transitory computer-readable storage medium having stored therein machine readable instructions to control a robot system and a memory configured to store pre-operative image data, the machine readable instructions, when executed by a processor, cause the processor to:
   communicate with the robot system having a controller and a robot with a rigid proximal portion and a flexible distal portion, the rigid proximal portion (i) comprising a portion through which to insert the flexible distal portion and (ii) having a pivot point configured to provide a plurality of degrees of freedom for movement of the rigid proximal portion at a pre-designated position in a surgical procedure;
   generate a first deployment path for the rigid proximal portion to follow from an entry location of a patient to an entry location to a region of interest within a surgical site of the patient;
   receive first tracking information indicating a tracked position of the rigid proximal portion;
   generate first guidance information for positioning the rigid proximal portion along the first deployment path based on the first tracking information, the received images, and the pre-operative image data;
   guide the rigid proximal portion on the first deployment path to be positioned at the entry location to the region of interest based on the first guidance information, wherein the rigid proximal portion is configured so that, when the rigid proximal portion is positioned at the first target position, the pivot point of the rigid proximal portion is located at the entry location to the region of interest enabling the rigid proximal portion to pivot around the entry location to the region of interest;
   deploy the flexible distal portion through the rigid proximal portion into the region of interest at the entry location to the region of interest;
   receive second tracking information indicating a tracked position of the flexible distal portion within the region of interest;
   generate a second deployment path for the deployed flexible distal portion to follow from the entry location to the region of interest to a target within the region of interest; and
   generate second guidance information for positioning the flexible distal portion along the second deployment path based on the second tracking information, the received images, and the pre-operative image data;
   guide, independently from guidance of the proximal rigid portion, the flexible distal portion on the second deployment path to the target within the region of interest.

15. The non-transitory computer-readable storage medium according to claim 14, wherein the machine readable instructions, when executed by the processor, cause the processor to:
- initially determine an initial position of the rigid proximal portion with respect to the patient; and
- register the rigid proximal portion to the region of interest in the surgical site of the patient,
- wherein the first deployment path is generated based on the registration of the rigid proximal portion.

16. The non-transitory computer-readable storage medium according to claim 14, wherein the machine readable instructions, when executed by the processor, cause the processor to:
- generate the first deployment path based on known locations of a first entry location of the rigid proximal portion into a body of the patient and of boundaries of the region of interest based on images provided by the at least one image acquisition device.

17. The non-transitory computer-readable storage medium according to claim 16, wherein the machine readable instructions, when executed by the processor, cause the processor to:
- generate the second deployment path based on known locations of a second entry location of the rigid proximal portion into the region of interest and of the target based on images provided by the at least one image acquisition device.

18. The non-transitory computer-readable storage medium according to claim 14, wherein the machine readable instructions, when executed by the processor, cause the processor to:
- transmit the images provided by the at last one image acquisition device to a display.

19. The non-transitory computer-readable storage medium according to claim 14, wherein tracking the position of the flexible distal portion within the region of interest comprises at least one of optical tracking, mechanical tracking, electromagnetic tracking system, and shape sensing tracking.

* * * * *